United States Patent
Tritthart

(10) Patent No.: US 11,007,363 B2
(45) Date of Patent: May 18, 2021

(54) IMPLANTABLE ELECTRODE WITH DEXAMETHASONE COATING

(71) Applicant: MED-EL Elektromedizinische Geraete GmbH, Innsbruck (AT)

(72) Inventor: Thomas Tritthart, Völs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 122 days.

(21) Appl. No.: 16/484,916

(22) PCT Filed: Feb. 7, 2018

(86) PCT No.: PCT/US2018/017150
§ 371 (c)(1),
(2) Date: Aug. 9, 2019

(87) PCT Pub. No.: WO2018/148230
PCT Pub. Date: Aug. 16, 2018

(65) Prior Publication Data
US 2019/0381309 A1    Dec. 19, 2019

Related U.S. Application Data

(60) Provisional application No. 62/456,741, filed on Feb. 9, 2017.

(51) Int. Cl.
*A61N 1/36* (2006.01)
*A61N 1/05* (2006.01)
*A61K 31/573* (2006.01)

(52) U.S. Cl.
CPC .......... *A61N 1/0541* (2013.01); *A61K 31/573* (2013.01); *A61N 1/0568* (2013.01); *A61N 1/36038* (2017.08)

(58) Field of Classification Search
CPC .............. A61N 1/0541; A61N 1/36038; A61N 1/0568; A61K 31/573
See application file for complete search history.

(56) References Cited

U.S. PATENT DOCUMENTS

| | | | |
|---|---|---|---|
| 2003/0054090 A1* | 3/2003 | Hansen | B05D 1/04 427/2.1 |
| 2007/0088335 A1 | 4/2007 | Jolly | |
| 2009/0062896 A1 | 3/2009 | Overstreet et al. | |
| 2009/0292237 A1 | 11/2009 | Overstreet et al. | |
| 2012/0141572 A1 | 6/2012 | Hessler et al. | |
| 2013/0079749 A1* | 3/2013 | Overstreet | A61M 31/00 604/514 |

OTHER PUBLICATIONS

European Patent Office, International Search Report and the Written Opinion of the International Searching Authority, Application No. PCT/US2018/017150, dated May 22, 2018, 13 pages.

* cited by examiner

*Primary Examiner* — Ankit D Tejani
*Assistant Examiner* — Joshua Brendon Solomon
(74) *Attorney, Agent, or Firm* — Sunstein LLP

(57) ABSTRACT

A method of forming an implantable electrode having electrode contacts on an electrode carrier having a coating includes providing a solution of silicone and dexamethasone dissolved in a solvent, applying the solution to the electrode carrier or to a substrate, and subjecting the solution to a two-step heat treatment process that includes a first heat treatment between about 50 and 90° C. for about 1 to 3 hours and a second heat treatment at an elevated temperature between 90° C. and 140° C. for about 2 hours in order to form the coating.

21 Claims, 3 Drawing Sheets

IMPLANTABLE ELECTRODE WITH DEXAMETHASONE COATING

CROSS-REFERENCE TO RELATED APPLICATIONS

This application is the national phase entry of International Patent Application No. PCT/US2018/017150 filed Feb. 7, 2018, which claims the benefit of U.S. Provisional Patent Application No. 62/456,741 filed Feb. 9, 2017, the disclosures of which are incorporated by reference herein in its their entirety.

TECHNICAL FIELD

The present invention relates to a method of forming an implantable electrode with a drug-filled coating, and more specifically to a method of forming an electrode with a silicone coating containing dexamethasone for a cochlear implant system.

BACKGROUND ART

Implantable auditory prostheses have been developed, such as cochlear implant systems, to improve impaired hearing in patients. In implantable systems, it is important to minimize the physical trauma caused by the insertion and placement of the stimulation electrode in order to reduce the risk of further hearing loss due to the insertion process itself. The use of a drug, before, during and/or after implantation, may help to minimize the trauma, and the stimulation electrode may be used to deliver the drug locally. For example, the stimulation electrode may be formed from a silicone material embedded with the drug or the silicone material may have a coating embedded with the drug so that the drug is released over time to the surrounding tissue. In some cases, however, it is difficult or not possible to control the release of the drug from the silicone or coating in a desired way.

U.S. Patent Appl. No. 2009/0197850 describes a coating containing a drug in a polymer. The release can be controlled by the degree of crystallinity of the polymer.

U.S. Patent Appl. No. 1997/010011 discloses a method for coating an implantable prostheses with a layer comprising an hydrophobic elastomeric material and a biologically active species by: applying a formulation containing polymeric material in solvent mixture and an amount of finely divided biologically active species; curing said polymeric material; and wherein the average particle size of the finely divided biological species in the coating formulation is selected to affect delivery kinetics. In general, the particle size is determined during the evaporation of the solvent.

U.S. Patent Appl. No. 20090197850 describes an implantable device that includes a drug, and a polymer layer having a crystalline structure, wherein the structure of the polymer becomes less crystalline when the polymer is exposed to an electric signal, and if the electric signal is terminated, the structure of the polymer returns back to essentially the same degree of crystallinity or a more crystalline structure than when the polymer was exposed to the electric signal.

FIG. 1 schematically shows some components of a typical cochlear implant system in a human ear. The cochlear implant system includes an external microphone which provides an audio signal input to an external signal processor 111 which implements one of various known signal processing schemes. The processed signal is converted by the external signal processor 111 into a digital data format, such as a sequence of data frames, for transmission by an external coil 107 into a receiving stimulator processor 108. Besides extracting the audio information, the receiving stimulator processor 108 may perform additional signal processing, such as error correction, pulse formation, etc., and produces a stimulation pattern (based on the extracted audio information) that is sent through to an implanted stimulation electrode. The stimulation electrode is typically made of a flexible silicone electrode carrier with wires embedded within the silicone that are connected to stimulation contacts on the surface of the carrier. The stimulation electrode includes an electrode lead 109 and an electrode array 110, which is gently inserted into the scala tympani of the cochlea 104. Typically, the electrode array 110 includes multiple stimulation contacts 112 distributed along its surface that provide selective electrical stimulation of the cochlea 104. The electrode contacts may also be used for sensing neural tissue response signals, e.g., the stimulation electrode may also function as a measurement electrode.

Other parts of the ear are also shown in FIG. 1. The ear usually transmits sounds, such as speech sounds, through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. The cochlea 104 forms an upright spiraling cone with a center called the modiolus where the axons of the auditory nerve 113 reside. In response to received sounds transmitted by the middle ear 103, the fluid-filled cochlea 104 functions as a transducer to convert mechanical motion and energy and, in response, to generate electric pulses which are transmitted to the auditory nerve 113, and ultimately to the brain. As mentioned above, in patients with a cochlear implant system, the implanted electrode array 110 provides the electrical stimulation to the cochlea 104.

SUMMARY OF EMBODIMENTS

In accordance with one embodiment of the invention, a method of forming an implantable electrode having electrode contacts on an electrode carrier having a coating includes providing a solution of silicone and dexamethasone dissolved in a solvent, applying the solution to the electrode carrier or to a substrate, and subjecting the solution to a two-step heat treatment process that includes a first heat treatment between about 50 and 90° C. for about 1 to 3 hours and a second heat treatment at an elevated temperature between about 90° C. and 140° C., preferably around 140° C., for about 2 hours in order to form the silicone coating.

In some embodiments, the coating may be applied directly on the electrode carrier. Alternatively, the coating may be applied onto a substrate. In this case, the coating may be transferred from the substrate to the electrode carrier or the coated substrate may be fixed to the electrode carrier. The solution may be applied using non-contact micro dispensing systems and/or contact dispensing systems. For example, the non-contact micro dispensing systems may be pipe jet dispensing systems, jet-forming dispensing systems, and/or dynamic drop dispensing systems. The coating may be in the shape of rings, lines, spots, or combinations thereof and may be applied between at least two electrode contacts. The electrode carrier may be formed from a Liquid Silicone Rubber or Low Consistency Elastomer having a durometer hardness measurement of between about 25 and 50 Shore A. The solution may be formed by dissolving silicone and dexamethasone in the solvent and adding a non-solvent to the solvent, the non-solvent miscible with the silicone, the dexamethasone having a solubility in the non-solvent of below about 5 mg/ml. The non-solvent may be added to the solvent to form a solvent mixture before dissolving the silicone and the dexamethasone in the solvent. In this case, the dexamethasone may be added to the solvent mixture and then the silicone may be added to the solvent mixture. Alternatively, the non-solvent may be added to the solvent after dissolving the silicone and the dexamethasone in the solvent. The non-solvent may be added in an amount of 10% or 5% by volume below the saturation of the dexamethasone in the solution. The total solid concentration may be between about 5% by weight to about 25% by weight in the solution. Preferably, the solution is kept slightly below the saturation point of dexamethasone. The concentration of the dexamethasone in the coating may be between about 1% by weight to about 20% by weight of the coating. The solvent may be tetrahydrofurane. The non-solvent may be unsubstituted or substituted aliphatic, cycloaliphatic or aromatic hydrocarbons. For example, the non-solvent may be n-hexane or isomers therefrom, n-pentane or isomers therefrom, cyclopentane, n-heptane or isomers therefrom, n-octane or isomers therefrom, n-nonane or isomers therefrom, n-decane or isomers therefrom, n-dodecane or isomers therefrom, benzene, toluene, and/or xylene.

The non-solvent may be n-hexane and the solvent may be tetrahydrofurane. In this case, the ratio of tetrahydrofurane to n-hexane by volume may be about 77/23 in the solution. The dexamethasone solubility in the non-solvent may be below about 1 mg/ml. The total solid concentration may be between about 6% by weight to about 10% by weight in the solution. The concentration of the dexamethasone in the silicone coating may be between about 10% by weight to about 20% by weight of the silicone coating. The solvent may be tetrahydrofurane. An implantable electrode may be formed according to any of the processes described above.

BRIEF DESCRIPTION OF THE DRAWINGS

The foregoing features of the embodiments will be more readily understood by reference to the following detailed description, taken with reference to the accompanying drawings, in which.

DESCRIPTION OF ILLUSTRATIVE
EMBODIMENTS

Various embodiments of the present invention provide a method of forming an electrode with a drug-filled silicone coating for a cochlear implant system in order to obtain a desired release rate of the drug, such as dexamethasone, and to cure the silicone coating. The method includes a heat treatment process for the silicone coating which allows control of the release rate of the dexamethasone or drug. Details of illustrative embodiments are discussed below.

Figure 1:
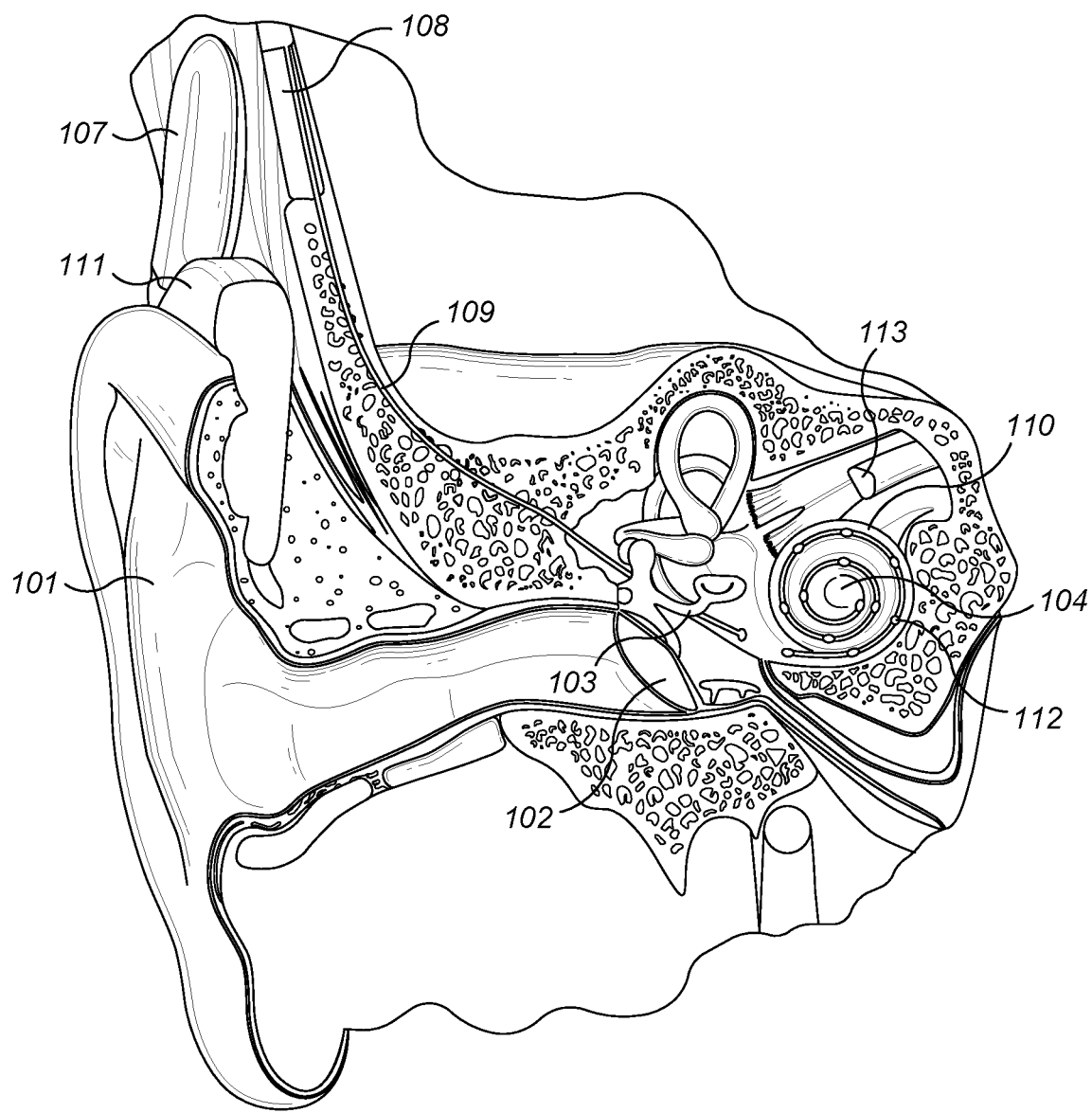
FIG. 1 shows anatomical structures of a human ear having a cochlear implant system.
Figure 2:
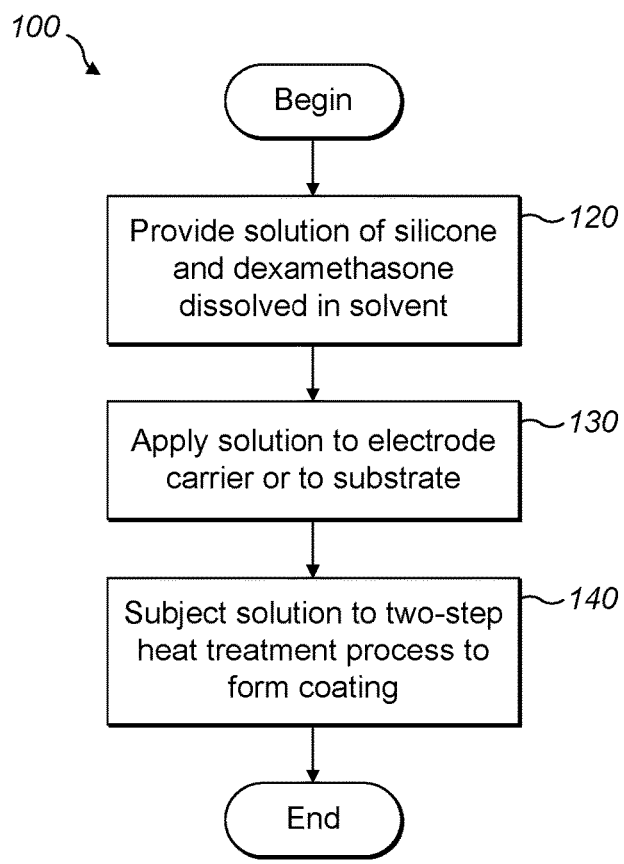
FIG. 2 shows a process of forming an electrode according to embodiments of the present invention.
Figure 3:
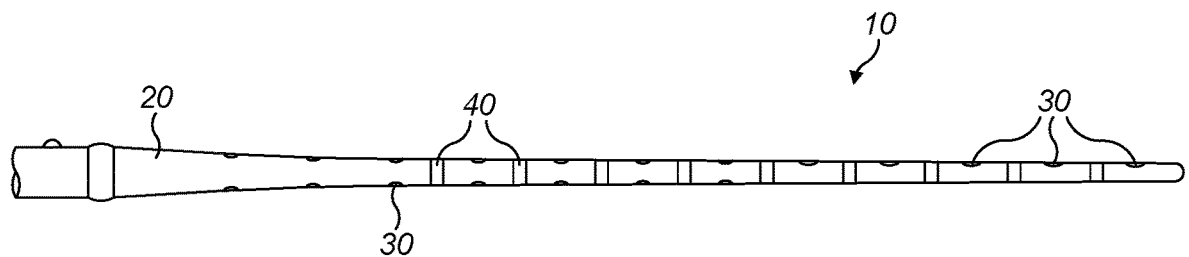
FIG. 3 shows an electrode formed according to embodiments of the present invention.

FIG. 2 shows a process 100 of forming an electrode 10 and FIG. 3 shows the electrode 10 formed by the process according to embodiments of the present invention. The process begins at step 120, in which a solution of silicone and dexamethasone dissolved in a solvent is provided. The solution is formed by dissolving both the silicone and the dexamethasone in an appropriate solvent in order to form a homogeneous and dispensable solution. The silicone may be a Liquid Silicone Rubber (LSR) or Low Consistency Elastomer, e.g., having a durometer hardness measurement of between about 25 to about 50 Shore A. For example, the silicone may be a two part addition curing silicone elastomer having a durometer measurement of about 25 to 50 Shore A and good self-adhesion to the electrode 10 with curing within about 1 hour at 100° C. For instance, the silicone may be formed from commercially available silicone MED-4244 (NuSil Technology LLC, Carpinteria, Calif.) or Liquid Silicone Rubber part no. 40082 (Applied Silicone Corporation, Santa Paula, Calif.) or an equivalent material.

The solution may include a non-solvent added to the solvent to form a solvent mixture, with the non-solvent being miscible with the silicone and being substantially immiscible with the dexamethasone. For example, the dexamethasone may have a solubility in the non-solvent of below about 5 mg/ml, and preferably below about 1 mg/ml. The solvent may be tetrahydrofurane (THF) and should be volatile. The non-solvent may be an unsubstituted or substituted aliphatic, cycloaliphatic or aromatic hydrocarbon, either branched or straight. For example, the non-solvent may be, preferably, n-hexane or isomers, n-pentane or isomers therefrom. Cyclopentane, n-heptane or isomers, n-octane or isomers, n-nonane or isomers, n-decane or isomers, n-dodecane or isomers therefrom, benzene, toluene, xylene and/or a mixture thereof. Preferably, the non-solvent also shows a low boiling point and high partial vapor pressure at room temperature. Therefore, n-hexane or n-pentane is preferably used over non-solvents of higher molecular mass. Finally, preferably, the vapor pressure is kept low at room temperature for the final solution. Non-solvents with a high boiling point and low partial vapor pressure might also result in a final mixture containing all components with high vapor pressure and therefore a quick evaporation of the solvent. In addition, the substrate may be heated to decrease the evaporation time when dispensed on the electrode carrier 20. For instance, the non-solvent may be n-hexane and the solvent may be THF. In this case, the ratio of THF to n-hexane by volume may be about 77/23 in the solution. The non-solvent may be added to the solvent before dissolving the silicone and the dexamethasone in the solvent. In this case, the dexamethasone may be added to the solvent mixture and then the silicone may be added to the solvent mixture. Alternatively, the non-solvent may be added to the solvent after dissolving the silicone and the dexamethasone in the solvent. The non-solvent may be added in an amount of 10% or 5% by volume below a saturation of the dexamethasone in the solution. The total solid concentration in the final solution may be in a range of about 6% by weight to about 30% by weight. Preferably, the solvent and non-solvent have a purity of at least 95%. A detailed description of a process of forming the dexamethasone coating may be found in patent application entitled DEXAMETHASONE COATING FOR USE WITH ELECTRODE CARRIER having No. 62/456,726 and filed on the same day herewith, which is incorporated by reference herein in its entirety.

In step 130, the solution is applied to an electrode carrier 20 of the electrode 10 or to a substrate. If the solution is applied to a substrate, then the coating may be transferred from the substrate to the electrode carrier or the substrate with the coating may be fixed to the electrode carrier. The electrode carrier 20 has a plurality of contacts 30 disposed on the electrode carrier 20 and may be formed from silicone. The solution may be applied in any shape on the electrode carrier 20. For example, the solution may be applied in the shape of rings, lines, or spots between one or more of the electrode contacts 30 or may be applied in a combination of rings, lines, and/or spots, e.g., a line in the apical region and rings between the contacts 30 in the basal region. As mentioned previously, the contacts 30 may be used to stimulate nerves and/or to record nerve impulses or potentials from the nerves. The electrode 10 may have an electrode lead electrically connecting the electrode 10 to a processor (not shown) for controlling the stimulation and/or recording of the electrode contacts 30. The processor may also provide signal processing capabilities to the stimulation and/or recording signal information. The solution may be applied to the electrode carrier 20 between one or more of the contacts 30 with a commercially available non-contacting micro dispensing system, such as pipe jet, jet-forming or dynamic drop dispensing (ink-jet) systems. Alternatively, the solution may be applied by contact dispensing. In a further alternative, the solution may be applied to the electrode carrier 20 by means of a peelable substrate, e.g., a polymeric foil coated with the solution. The solution may be applied to the substrate by any of the above mentioned methods. In addition, the solution may be applied to the substrate by immersing the substrate into the solution. The prepared substrate coated with the solution may be gently pressed against the electrode carrier 20.

In step 140, the electrode carrier 20, the electrode carrier 20 with gently pressed substrate, substrate with solution, or substrate with solution that will be a part or parts fixated to the electrode carrier 20 is subjected to a two-step heat treatment process to cure the solution into a silicone coating 40 and to form the electrode 10 or coated substrate respectively. Most of the solvent may be evaporated from the solution at room temperature first and then the silicone may be cured in an oven with specific temperature settings. The heat treatment includes a first heat treatment below 90° C. for about 1 to 3 hours and then a second heat treatment at an elevated temperature to help cure the silicone completely. In one embodiment, the temperature of the second heat treatment may be elevated by at least about 5° C., preferable 10° C. and further preferable 20° C. For example, the first heat treatment may be between about 50-90° C. for about 1 to 3 hours and the second heat treatment may be between about 90° C. and 140° C., and preferably around 140° C., for about 2 hours. For example, the silicone coating 40 may be cured for about 1 to 3 hours at 70° C. with an additional curing step at about 140° C. for 2 hours. With the two-step heat treatment, the release rate of the dexamethasone can be controlled simply with the temperature of curing. After heat curing and when a peelable substrate is pressed onto the electrode carrier 20 in step 130, the substrate may be easily peeled off from the electrode carrier 20 while the coating remains on the electrode carrier 20. The substrate may be peeled off (1) after the first heat treatment and before the second heat treatment, (2) immediately after the second heat treatment or (3) after the second heat treatment and cooling down to a certain temperature, e.g. room temperature. If only the substrate with solution is heat cured, the coated substrate after heat treatment may be gently pressed onto the electrode carrier 20 and, by peeling off the substrate, the coating 40 remains on the electrode carrier 20. For this purpose, use of adhesive may help to transfer the coating 40 from the substrate onto the electrode 10.

The coating 40 is preferably formed from a silicone material because silicone is a material known for releasing embedded drugs, e.g., steroids, is biostable, biocompatible, resistant to sterilization procedures and has the desired properties in terms of elasticity, so that the flexibility of the final, coated electrode 10 is not adversely affected. The silicone coating 40 should have good adhesion to the underlying silicone substrate (i.e., the silicone body of the electrode carrier 20). The coating 40 should also be able to withstand being implanted for a long term. In order to increase the drug release rate, the silicone coating 40 may be loaded with dexamethasone at greater than 10% by weight, e.g., in the range of about 15% by weight to about 20% by weight of dexamethasone in the silicone coating when using an addition curing LSR silicone or Low Consistency Elastomer silicone, e.g., with a durometer of about 40 Shore A. Above 20% by weight, the solution tends to form agglomerates when coated on the electrode carrier 20.

It is understood that the steps described above may be equally applied to parts that may, after step 140, be fixated to the electrode carrier 20 by means of mechanical fixations or by use of adhesive. Such parts may be formed of various suitable shapes, for example as rings that can be placed over the electrode carrier 20. Using such parts or a substrate to transfer the coating 40 has the advantage that the quality of the coating 40 can be quantified before application to the electrode carrier 20. This significantly reduces the production process risks and avoids unnecessary and expensive rejects of implant devices due to insufficient coating quality.

A coating 40 manufactured according to embodiments of the invention has a surface roughness that is typical for the various production methods (e.g., surface roughness arising from the mold itself) without additional surface roughness caused by the additional of the dexamethasone in the silicone coating t. This is mainly because the liquid solution readily distributes over the surface before becoming final shape during curing. Further, the surface of the silicone with the coating does not show adhesive properties, which is typically the case for silicone (for example, silicone feels slightly sticky or tacky when touched). A thin coating, e.g., of 100 μm thickness, distributed uniformly over the surface with the dexamethasone can only be obtained by dispensing a fluid, for example, with a solution according to embodiments of the invention.

As used herein, the term applying a coating to the electrode carrier includes all the above described methods and without limitation includes transfer by a peelable substrate, fixated and coated parts. As used herein, the term "or" used in connection with a list of items, means one or more of the items in the list, but not necessarily all of the items in the list.

EXAMPLES

A set of experiments were conducted to show the feasibility of the processing parameters used to form the electrode with the dexamethasone coating composition according to embodiments of the present invention.

Example 1

The coatings were prepared by forming a solution of n-hexane and THF at 23% by volume and then adding dexamethasone to get a concentration of 1.38% by weight. Mixed silicone (PART A and PART B) of MED 1-4244 was added in a concentration of 7.81% by weight. The solution was dispensed with a micro dispensing system to give 9 rings between the contact plates with about 105 µg of coating. The experiment was carried out in an environmentally controlled area with a temperature around 23° C. and 48% to 51% humidity.

Three coated electrodes were then subjected to each of the following two heat treatment parameters:

Heat Treatment A—3 electrodes for 1 hour at 70° C. and 2 hours at 140°; and

Heat Treatment B—3 electrodes for 2 hours 140°.

The release rate of the drug for Heat Treatment A yielded about 860 ng/d for the first 0-100 hrs. and about 216 ng/d for 100-500 hrs. The release rate of the drug for Heat Treatment B yielded about 565 ng/d for the first 0-100 hrs. and about 150 ng/d for 100-500 hrs. Therefore, the release rate of the dexamethasone was increased by about 50% within the first 4 days and about 44% from day 4 to day 21, by just including a two-step heat treatment process according to embodiments of the present invention.

Example 2

The coatings were prepared by forming a solution of n-hexane and THF at 23% by volume and then adding dexamethasone to get a concentration of 1.38% by weight. Mixed silicone (PART A and PART B) of MED 1-4244 was added in a concentration of 7.81% by weight. The solution was dispensed with a micro dispensing system to give 9 rings between the contact plates with about 105 µg of coating. The experiment was carried out in an environmentally controlled area with a temperature around 23° C. and 48% to 51% humidity.

Three coated electrodes were then subjected to each of the following heat treatment parameters:

Heat Treatment A—3 electrodes for 3 hours at 70° C. and 2 hours at 140° C.;

Heat Treatment B—3 electrodes for 1 hour at 70° C. and 2 hours at 140° C.; and

Heat Treatment C—3 electrodes for 2 hours at 140° C.

Figure 4:
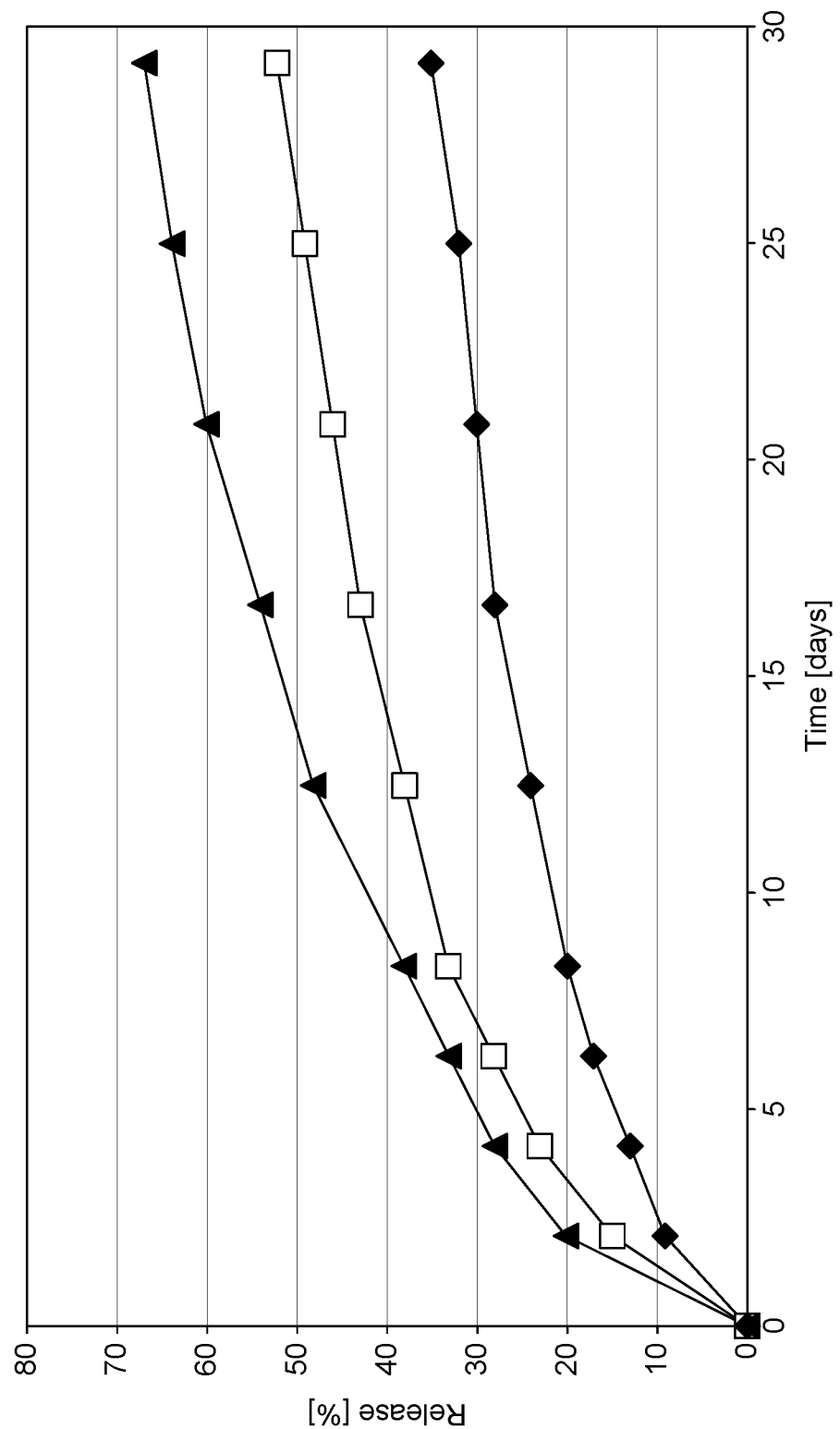
FIG. 4 is a graph showing the release rate as a function of time for three heat treatment processes according to embodiments of the present invention.

A graph of the release rate of the drug as a function of time is shown in FIG. 4 for the three sets of heat treatment parameters. Heat Treatment A is the upper curve (triangles), Heat Treatment B is the middle curve (squares), and Heat Treatment C is the bottom curve (diamonds).

Although the above discussion discloses various exemplary embodiments, those skilled in the art may make various modifications to, or variations of, the illustrated embodiments without departing from the inventive concepts disclosed herein.

What is claimed is:

1. A method of forming an implantable electrode having electrode contacts on an electrode carrier having a coating, the method comprising:
providing a solution of silicone and dexamethasone dissolved in a solvent;
applying the solution to the electrode carrier or to a substrate; and
subjecting the solution to a two-step heat treatment process that includes a first heat treatment between 50° C. and 90° C. for about 1 to 3 hours and a second heat treatment at an elevated temperature between about 90° C. and 140° C. for about 2 hours in order to form the coating.

2. The method of claim 1, wherein the coating is applied directly on the electrode carrier.

3. The method of claim 1, wherein the coating is applied onto the substrate, the method further comprising transferring the coating from the substrate to the electrode carrier.

4. The method of claim 1, wherein the coating is applied onto the substrate, the method further comprising fixing the coated substrate to the electrode carrier.

5. The method of claim 1, wherein the solution is applied using non-contact micro dispensing systems or contact dispensing systems.

6. The method of claim 5, wherein the non-contact micro dispensing systems include pipe jet dispensing systems, jet-forming dispensing systems, dynamic drop dispensing systems, or combinations thereof.

7. The method of claim 1, wherein the coating is applied to the electrode carrier or to the substrate in the shape of rings, lines, spots, or combinations thereof and applied between at least two electrode contacts.

8. The method of claim 1, wherein the solution is formed by dissolving silicone and dexamethasone in the solvent and adding a non-solvent to the solvent, the non-solvent miscible with the silicone, the dexamethasone having a solubility in the non-solvent of below about 5 mg/ml.

9. The method of claim 8, wherein the non-solvent is added to the solvent to form a solvent mixture before dissolving the silicone and the dexamethasone in the solvent.

10. The method of claim 9, wherein the dexamethasone is added to the solvent mixture and then the silicone is added to the solvent mixture.

11. The method of claim 8, wherein the non-solvent is added to the solvent after dissolving the silicone and the dexamethasone in the solvent.

12. The method of claim 8, wherein the non-solvent is added in an amount of 10% by volume below a saturation of the dexamethasone in the solution.

13. The method of claim 8, wherein the non-solvent is added in an amount of 5% by volume below a saturation of the dexamethasone in the solution.

14. The method of claim 8, wherein the non-solvent includes unsubstituted or substituted aliphatic, cycloaliphatic or aromatic hydrocarbons.

15. The method of claim 14, wherein the non-solvent includes n-hexane or isomers therefrom, n-pentane or isomers therefrom, cyclopentane, n-heptane or isomers therefrom, n-octane or isomers therefrom, n-nonane or isomers therefrom, n-decane or isomers therefrom, n-dodecane or isomers therefrom, benzene, toluene, xylene or combinations thereof.

16. The method of claim 8, wherein the non-solvent is n-hexane and the solvent is tetrahydrofurane, and the ratio of tetrahydrofurane to n-hexane by volume is about 77/23 in the solution.

17. The method of claim 8, wherein the dexamethasone solubility in the non-solvent is below about 1 mg/ml.

18. The method of claim 1, wherein total solid concentration is between about 6% by weight to about 10% by weight in the solution.

19. The method of claim 1, wherein concentration of the dexamethasone in the coating is between about 10% by weight to about 20% by weight of the coating.

20. The method of claim 1, wherein the solvent includes tetrahydrofurane.

21. An implantable electrode formed according to the method of claim 1.

* * * * *